(12) United States Patent
Li et al.

(10) Patent No.: US 6,654,109 B2
(45) Date of Patent: Nov. 25, 2003

(54) SYSTEM FOR DETECTING SURFACE DEFECTS IN SEMICONDUCTOR WAFERS

(75) Inventors: Lain-Jong Li, Hualien (TW); Chung-Chi Ko, Nanton (TW); Syun-Ming Jang, Hsin-Chu (TW)

(73) Assignee: Taiwan Semiconductor Manufacturing Co. Ltd, Hsin Chu (TW)

( * ) Notice: Subject to any disclaimer, the term of this patent is extended or adjusted under 35 U.S.C. 154(b) by 0 days.

(21) Appl. No.: 10/068,417

(22) Filed: Feb. 5, 2002

(65) Prior Publication Data

US 2003/0147069 A1 Aug. 7, 2003

(51) Int. Cl.[7] .............................................. C01N 21/88
(52) U.S. Cl. .................................................. 356/237.2
(58) Field of Search ........................ 356/237.2, 237.3, 356/237.4, 237.5, 446, 600

(56) References Cited

U.S. PATENT DOCUMENTS 5,153,668 A * 10/1992 Katzir et al. .............. 356/237.2
6,078,386 A * 6/2000 Tsai et al. ................. 356/237.1

* cited by examiner

Primary Examiner—Richard A. Rosenberger
(74) Attorney, Agent, or Firm—Tung & Associates

(57) ABSTRACT

Defects such as holes and bumps in the surface of a semiconductor wafer are detected by an optical inspection system that combines darkfield and brightfield illumination techniques. A single light stop, which forms part of the illumination system, includes a pair of openings configured to produce both a solid cone of light and a hollow of light which are simultaneously focused onto the wafer surface. The directly emanating light as well as the scattered light collected from the wafer surface produce a resultant image that is the product of darkfield and brightfield illumination. Modulation of the light beam and tilting of the light focused onto the wafer surface may be advantageously used to improved contrast and resolution of the viewed image.

15 Claims, 3 Drawing Sheets

SYSTEM FOR DETECTING SURFACE DEFECTS IN SEMICONDUCTOR WAFERS

TECHNICAL FIELD

The present invention broadly relates to methods and apparatus for inspecting surface features of objects, and deals more particularly with a system for detecting surface defects such as holes and bumps in the surface of a semiconductor wafer.

BACKGROUND ART

In the semiconductor manufacturing industry, maintaining and improving yield is an increasingly greater challenge as circuit designs become increasingly smaller. Foreign particles and process defects can seriously limit yields during the manufacturing of semiconductor wafers, consequently a great deal of resources has been directed toward developing sophisticated inspection systems for detecting particles and surface defects at the earliest possible stage during wafer fabrication. When the inspection process indicates a number of defects, the wafer may be sent back for re-cleaning. If the defects are particles or other debris on the wafer surface, the re-cleaning process is often successful. However if the defects consist of holes or bumps inherent in the wafer surface they may not be removed by re-cleaning. Because such surface inspection systems fail to distinguish between pit defects and particle defects the wafer is typically sent back for re-cleaning regardless of whether the defects are holes or particles.

Defects in the form of structural flaws, process residues and external contamination occur during the production of semiconductor wafers on a fairly routine basis. The defects are typically detected by a class of instruments referred to as defect scanners. These instruments automatically scan wafer surfaces and detect optical anomalies using a variety of techniques. The location of these anomalies with respect to the pattern of semiconductor devices on the wafer surface is recorded, and this information is often stored and accumulated to form a defect map. This map enables a human operator to systematically inspect each defect under a microscope so that the defect can be characterized according to type (particle, hole, scratch or contaminate). Information gained from this inspection process is then used to correct the source of the defects, and thereby improve efficiency and yield of the semiconductor commercial process.

The inspection process performed by a human operator utilizes a conventional optical microscope, or a much more complicated scanning electron microscope. The wafer is illuminated using any of a variety of techniques, including brightfield illumination, darkfield illumination or spatial illumination filtering. Brightfield illumination of the wafer involves lighting the specimen with a solid cone of rays. The transmitted brightfield illumination is normally performed by a sub-stage condenser and the reflected brightlight illumination is performed by a vertical illuminator. In brightfield illumination, the specimen appears dark against a light background. Brightfield imaging tends to scatter small particles away from the collecting aperture which results in reduced returned energy. When a particle is small compared to the optical point spread function of the lens and is small compared to the digitizing pixels, the brightfield energy from the immediate area surrounding the particle typically contributes a large amount of energy. The small reduction in return energy resulting from the small particles makes the particle difficult to detect. Further, the reduced level of return energy from small particles is often masked out by reflectivity variations from the bright surrounding background such that small particles cannot be detected without numerous false detections. Additionally, if the small particle is on an area of low reflectivity, which may occur for some process layers on wafers, the resultant background return is low and any further reduction due to the presence of a particle becomes thus very difficult to detect.

Brightfield microscopy apparatus relies upon light from a lamp source being gathered by the sub-stage condenser and shaped into a cone whose apex is focused at the plane of the specimen (wafer surface). Specimens are seen because of their ability to change the speed and path of the light passing through them. This ability is dependent on upon the refraction index and opacity of the specimen. To see a specimen in a brightfield microscope, the light rays passing through it must be changed sufficiently to be able to interfere with each other, which produces contrast (differences in light intensities) and thereby builds an image. If the specimen has a refraction index similar to the surrounding medium between the microscope stage in the objective lens, it will not be seen. If the wafer surface defect and the area surrounding the defect do not possess the proper refractive indices, the defect will not have sufficient contrast to be seen.

Darkfield microscopy relies on a different illumination system. Rather than illuminating the sample with a solid cone of light, the condenser is designed to form a hollow cone of light. The light at the apex of the cone is focused at the plane of the specimen; as this light moves past the specimen plane it spreads again into it a hollow cone. The objective lens sits in a dark hollow of this cone (although the light travels around and past the objective lens, no rays enter it). The entire field appears dark when there is no sample on the microscope stage, thus the name "darkfield microscopy". When a sample is on the stage, the light at the apex of the cone strikes it. The image is made only by those rays scattered by the sample and captured in the objective lens. The image appears bright against a dark background. The advantage of the darkfield imaging is that flat specular areas scatter very little light back toward the detector, resulting in a dark image. Darkfield illumination provides a larger pixel to defect ratio, permitting faster inspections for a given defect size and pixel weight. Darkfield imaging also permits the Fourier filtering to enhance signal to noise ratios.

Any surface features or objects protruding above the surface of the wafer scatter more light toward the detector in darkfield imaging. Darkfield imaging thus produces a dark damage except where circuit features or particles or other irregularities exist.

From the above, it is apparent that brightfield and darkfield microscopy each have their own advantages in detecting certain surface defects, but neither is effective in detecting the full range of defects that can occur on the surface of a semiconductor wafer. In the past, it has been particularly difficult to detect both "bumps" and holes" in the surface of a wafer using only one type of microscopy, i.e. darkfield or brightfield. It would therefore be desirable to provide an improved optical inspection system that utilizes an illumination system capable of revealing both bumps and holes in a wafer surface. The present invention is directed toward satisfying this need.

SUMMARY OF THE INVENTION

According to one aspect of the invention, an optical inspection system for detecting defects in the surface of a semiconductor wafer is provided comprising a light source, an optical assembly for illuminating the wafer, and an objective for collecting light from the wafer and forming a resultant image. The optical assembly includes components that produce simultaneous darkfield and brightfield illumination of the wafer surface. The objective collects both light scattered from the wafer as a result of the darkfield illumination, and light which passes directly through the wafer as a result of the brightfield illumination. The optical assembly includes a light stop having a central circular opening for allowing a beam of light to pass therethrough which is used to provide brightfield illumination, and a ring-shaped opening concentrically disposed around a central opening. The ring-shaped opening allows a hollow cylinder of light to pass through the stop, which is used to produce darkfield illumination of the wafer. A condenser focuses both the hollow cone of light and the light beam substantially at the plane of the wafer surface. Light rays from the beam are refracted through the wafer and pass then directly into an objective lens. Scattered light from the wafer surface produced by the darkfield illumination is also received by the objective lens which forms an image of the wafer surface produced by both types of illumination. In a preferred embodiment, the illumination system is modulated by varying the size of the brightfield light beam and/or by tilting the illumination system relative to the wafer surface in order to improve contrast and the likelihood of detecting surface defects.

According to another aspect of the invention, a method is provided for detecting defects on the surface of a semiconductor wafer, comprising the steps of producing mixedfield illumination of the image of the wafer surface by simultaneously forming darkfield and brightfield illumination of the wafer surface, and viewing the mixedfield image. A darkfield image is formed by illuminating the wafer surface with a hollow cone of light and then collecting light scattered from the surface of the wafer. The brightfield image is formed by focusing solid cone or beam of light on the wafer surface and then collecting light emanating from the surface which originates from the beam. The hollow cone of light and the solid beam are preferably formed by passing light from a source thereof through openings in a single, opaque light stop. The method further includes the step of tilting the hollow cone of light and the solid light beam relative to the wafer surface, and modulating the light beam by changing the size of the beam.

Accordingly, it is the primary object of the present invention to provide an optical inspection system for detecting a wide range of defects in the surface of a semiconductor wafer, including bumps and holes or pits.

Another object of the invention is to provide a system as described above which simultaneously utilizes both brightfield and darkfield illumination of the wafer being inspected.

A further object of the invention is to provide a system as described above which possesses a minimum number of components, including a single light stop and a single source of illumination.

A still further object of the invention is to provide an inspection system of the type mentioned above which allows for modulation of the illumination system so as to maximize the probability of detecting surface defects.

These, and further objects and advantages of the present invention will be made clear or will become apparent during the course of the following description of a preferred embodiment of the present invention.

BRIEF DESCRIPTION OF THE DRAWINGS

In the drawings which form an integral part of the specification and are to be read in conjunction therewith, and in which like reference numerals are employed to designate identical components in the various views.

DESCRIPTION OF THE PREFERRED EMBODIMENT

Figure 1:
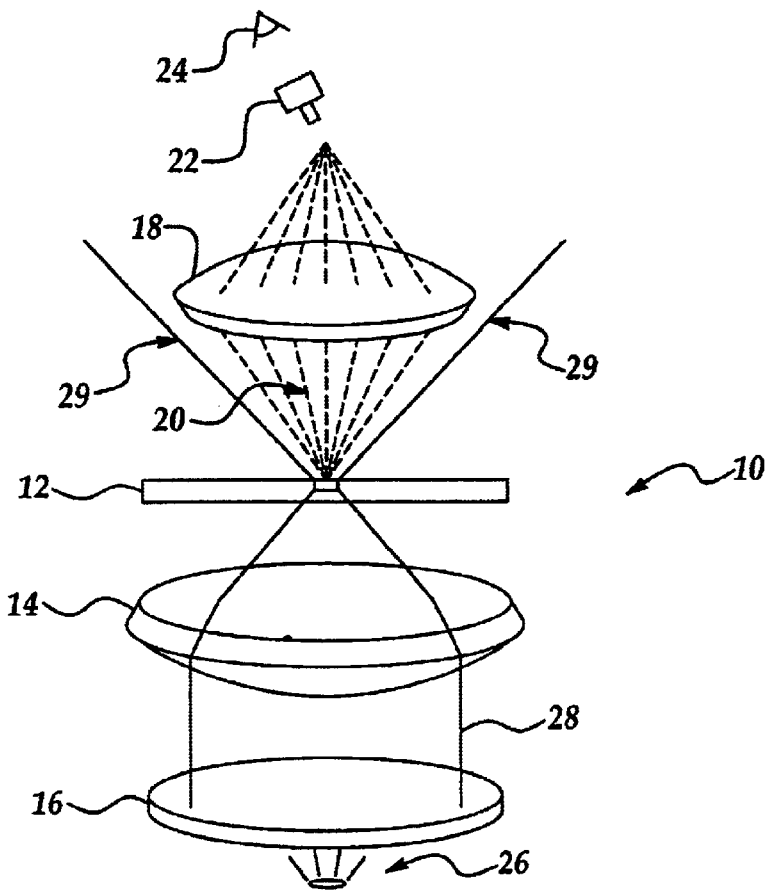
FIG. 1 is an exploded, diagrammatic view of a prior art wafer inspection system utilizing darkfield illumination.

Reference is first made to FIG. 1 which depicts an optical inspection system generally indicated by the numeral 10 which utilizes a prior art, darkfield illumination system. A conventional source of light 26 is directed toward a conventional light stop 16 which consists of an opaque, flat disk 16 having a ring-shaped opening near its outer periphery which allows a cylindrical ring 28 of light from the source to pass through the stop 16 to a condenser 14. The condenser 14 forms this cylindrical ring of light into a hollow cone which is directed toward and focused at the plane of the wafer 12 to be the inspected. This hollow cone of light passes through the transparent wafer 12 and forms an exiting hollow cone of light 29 which passes around and does not enter an objective lens 18. However, some light from the upper surface of wafer 12 is scattered, and this scattered light shown at 20 enters the objective lens 18 which focuses the scattered light into a darkfield image which is picked up by an eye-piece 22 viewed by a human operator 24. The resulting image viewed by the operator 24 is that of a darkfield image in which surface defects such as particles are theoretically seen as lighter features on an otherwise dark background. Whether these types of surface defects can in fact be actually seen, and the clarity with which they are seen, is dependent upon a number of factors including the geometry of the particle and its refractive index relative to that of the surrounding wafer material. Thus, surface features such as foreign particles or holes may or may not be detected with the prior art darkfield illumination technique. More significantly, however, darkfield illumination of the wafer surface will prove largely ineffective in allowing the operator 24 to detect holes or pits in the wafer surface 12. Conversely, prior art brightfield illumination systems tend to be more effective in detecting holes in wafer surfaces, and less effective in detecting foreign particles and bumps in wafer surfaces, as will become apparent later in this description.

Figure 2:
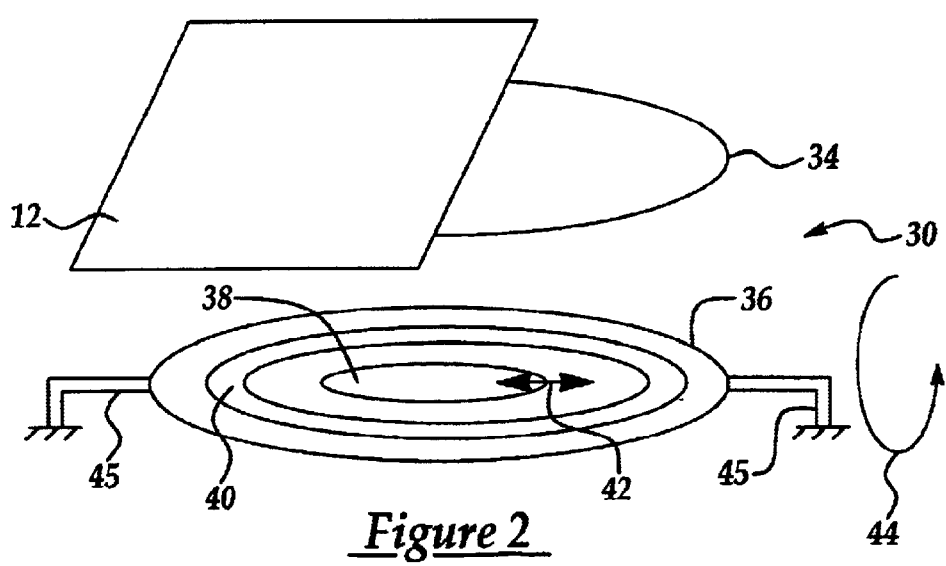
FIG. 2 is an exploded diagrammatic view of the inspection system which forms the preferred embodiment of the present invention.

The present invention stems in part from recognition that it is advantageous to combine both brightfield and darkfield illumination in the same inspection system in order to maximize the probability of detecting surface defects on the wafer. This is accomplished using a novel method and certain novel apparatus, which are shown in FIG. 2. A novel light stop 36 preferably in the form of a metal disk includes a central circular aperture 38, and an outer ring-shaped aperture 40 concentrically disposed around the aperture 38. Light stop 36 replaces the prior art light stop 16 shown in FIG. 1. The ring-shaped aperture 40 is identical to that shown in light stop 16 of FIG. 1, and thus allows a cylindrical ring of light to pass through the light stop 36 from the source 26 into the condenser 14 where it is converted into a hollow cone of light, as previously described. However, using the same light stop 36, light from the same source 26 passes through the central aperture 38 to form a solid central beam of light which is focused by condenser 14 at the plane of the wafer 12. This focused beam passes through the transparent wafer 12, and the emanating, refracted beam pattern is directed upwardly so as to fill the objective lens 18. Thus, it may be appreciated that the objective lens 18 receives both scattered light from the wafer surface resulting from the darkfield illumination of the wafer 12, as well as the refracted light beam which originates from the aperture 38 and passes through the body of the wafer 12. The term "mixedfield" will be used herein to refer to the dual, simultaneous darkfield and brightfield illumination of the wafer in accordance with the present invention.

Figure 7:
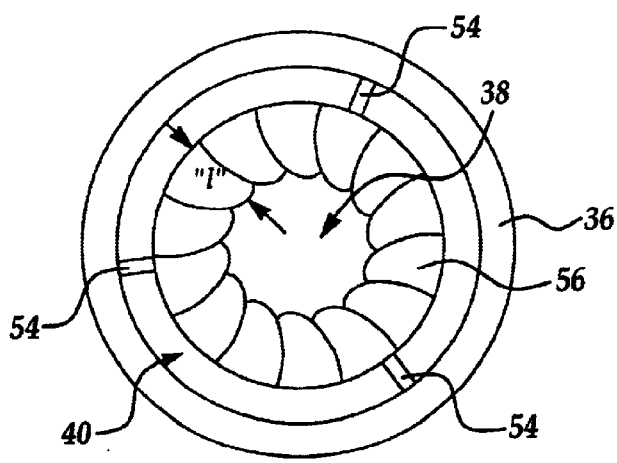

Referring also to FIG. 7, the light stop 36 may be formed such that the ring-shaped opaque material between the inner aperture 38 and the outer aperture 40 is in the form of a spider connected by radially spaced struts 54 which secure the spider to the outer ring-shaped periphery of the stop 36. In a preferred embodiment, the inner ring of opaque material 56 possesses a radially width "1" and can be adjusted so as to change the diameter of the light beam passing therethrough and thus modulate the light beam. This radial adjustment may be accomplished using any of a number of mechanisms, including a conventional iris-like arrangement of movable elements as shown in FIG. 7. Referring again to FIG. 2, light passing through the stop 36 is delivered through a filter 34 such as a polarizing filter to enhance the light illuminating the wafer 12. In a preferred form, the light stop 36 can be tilted in the direction of the arrow 44, relative to the plane of the wafer 12 so as to vary the angle of incidence of the light illuminating the wafer 12. The technique of tilting the source of illumination and modulating the diameter of the brightfield illumination beam has been found to substantially enhance inspection results, and the likelihood of detecting bumps and holes in the wafer surface. The light stop may be mounted on any of various mechanisms to accomplish tilting thereof including a simple mounting arrangement as shown in FIG. 2 in which the stop 36 is journaled for rotation about a pair of opposing the stationery arms 45.

Figure 3:
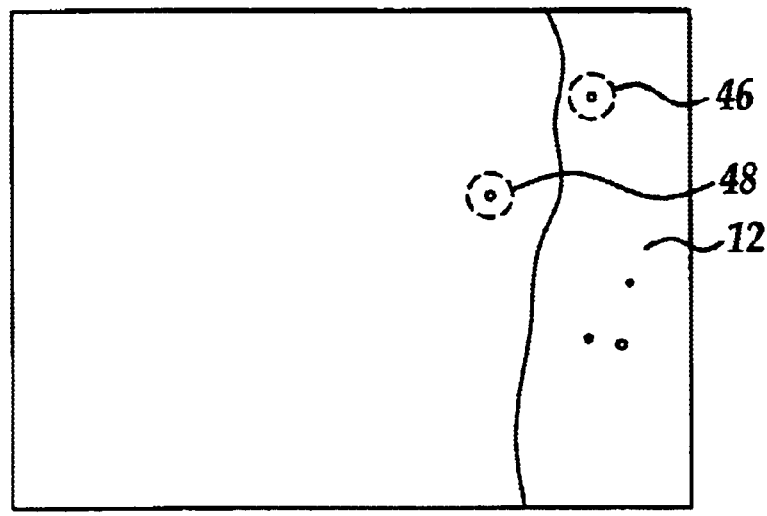
FIG. 3 is a microphotograph of an image of a wafer surface showing certain surface defects, using the prior art inspection system shown in FIG. 1.

FIG. 3 is a photomicrograph of the surface of a wafer illuminated only with a prior art brightfield illumination system. The particular wafer shown in FIG. 3 possesses both a bump and a hole respectively in the areas designated as 46 and 48, however, the hole is not clearly visible using a conventional microscope as evidenced by FIG. 3.

Figure 4:
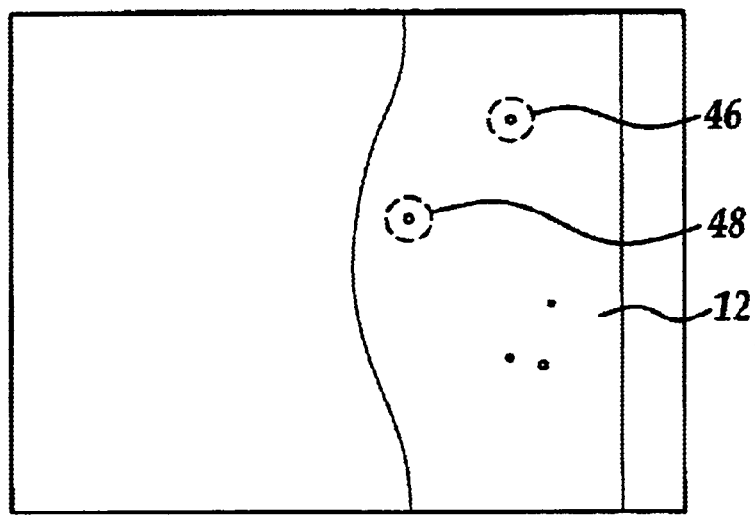
FIG. 4 is a microphotograph of the wafer shown in FIG. 3 using the mixedfield illumination of the present invention.

FIG. 4 is a photomicrograph of the same wafer surface shown in FIG. 3 taken at the identical level of magnification (200x) using a conventional optical microscope, but using the mixedfield illumination system of the present invention. It can be seen that both the bump 46 and the hole 48 are clearly visible.

Figure 5:
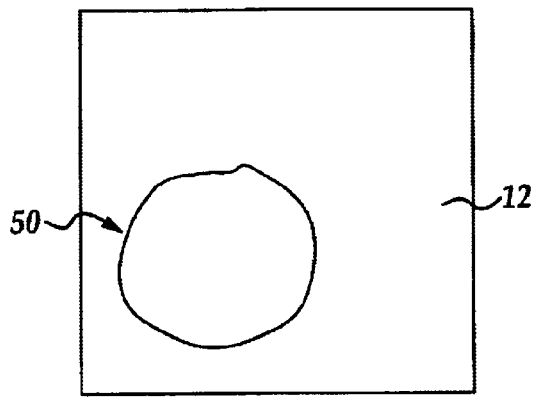
FIG. 5 is a microphotograph representing an enlarged view of a portion of the wafer surface shown in FIG. 4 which depicts a hole in the wafer surface.
Figure 6:
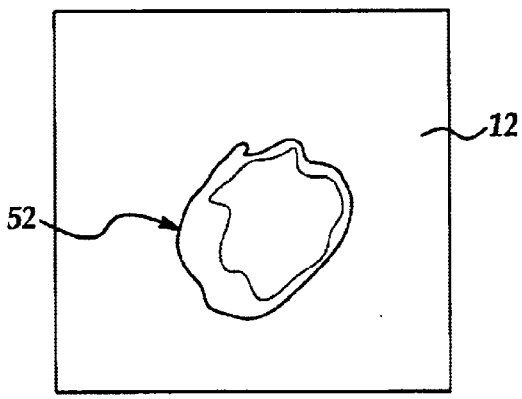
FIG. 6 is a microphotograph similar to FIG. 5 but depicting another area on the surface of the wafer shown in FIG. 4 and revealing a bump; and, FIG. 7 is a diagrammatic, plan view of the light stop shown in FIG. 2.

FIGS. 5 and 6 are photomicrographs taken with the use of a scanning electron microscope and respectively showing, on a much enlarged scale, the areas 46 and 48 of the wafer shown in FIGS. 3 and 4. As shown in FIG. 5, the outline of a hole designated by the numeral 50 can be clearly seen.

Similarly, as seen in FIG. 6, the outline of a bump 52 present in the area 48 in FIGS. 3 and 4 is clearly visible.

From the foregoing, it is apparent that the optical inspection system described above not only provides for the reliable accomplishment of the objects of the invention, but does so in a particularly effective and economic manner. It is recognized, of course, that those skilled in the art may make various modifications or additions chosen to illustrate the invention without departing from the spirit and scope of the present contribution to the art. Accordingly, it is to be understood that the protection sought and to be afforded hereby should be deemed to extend to the subject matter claimed and all equivalents thereof fairly within the scope of the invention.

What is claimed is:

1. An optical inspection system for detecting defects in the surface of a semiconductor wafer comprising:
    a source of light positioned to direct light toward said wafer;
    an optical assembly disposed between said light source and said wafer for simultaneously producing darkfield and brightfield illumination of said wafer, said optical assembly including an opaque light stop having first and second concentric openings therethrough, said first opening allowing a ring of light to pass therethrough for use in said darkfield illumination, said second opening allowing a solid beam of light to pass therethrough for use in said brightfield illumination; and
    an objective for collecting both light scattered from said wafer as a result of said darkfield illumination and light directly passing through said wafer as a result of said brightfield illumination.

2. The optical inspection system of claim 1, wherein said optical assembly includes a condenser for forming a hollow cone-shaped beam of light having a focal point essentially in the plane of said wafer.

3. The optical inspection system of claim 1, wherein said light stop includes an adjustable portion for allowing alteration of the width of said beam.

4. The optical inspection system of claim 3, wherein said adjustable portion includes a radially movable iris.

5. The optical inspection system of claim 1, wherein said first opening is ring shaped and surrounds said second opening.

6. The optical inspection system of claim 1, including an eyepiece for collecting light passing through said objective and forming an image of said wafer surface.

7. The optical inspection system of claim 1, wherein said light stop is mounted for tilting movement relative to said wafer.

8. An optical inspection system for detecting defects in the surface of a transparent object, comprising:
    a light source;
    an optical assembly for simultaneously illuminating said surface using a hollow cone of light and a solid cone of light, said optical assembly including a light stop having a central opening therein for forming said solid cone of light, and an outer ring shaped opening therein concentrically surrounding said central opening for forming said hollow cone of light;
    an objective for collecting both light scattered from said surface as a result of illumination of said surface with said hollow cone of light, and light directly passing through said wafer as a result of illumination of said surface with said solid cone of light; and
    an optical element for forming an image of said surface, said image being form by the combination of a darkfield image and a brightfield image.

9. The optical inspection system of claim 8, wherein said optical assembly includes a condenser for focusing said solid cone of light and said hollow cone of light essentially at the plane of said surface.

10. The optical inspection system of claim 8, wherein said light stop includes an adjustable portion for adjusting the width of said solid cone of light.

11. The optical inspection system of claim 8, wherein said light stop is mounted on a supporting surface for tilting movement relative to said object.

12. A method of detecting defects in the surface of semiconductor wafer, comprising the steps of:

(A) generating a mixedfield image of said surface by simultaneously forming darkfield and brightfield images of said wafer surface, said darkfield image being formed by illuminating said surface with a hollow cone of light, and collecting light scattered from the surface of said wafer, and said brightfield image being formed by focusing a solid cone of light on said wafer surface, and collecting light emanating from said surface and originating from said solid cone, said hollow cone of light and said solid cone of light being formed by passing light from a source thereof through openings in a single opaque light stop; and (B) viewing said mixedfield image.

13. The method of claim 12, including the step of tilting said light stop relative to said wafer surface.

14. The method of claim 12, wherein step (A) includes focusing said hollow cone of light and said solid cone of light on said wafer.

15. The method of claim 12, wherein step (A) includes modulating said solid cone of light by changing the width of said solid cone.

* * * * *